(12) United States Patent
Lai et al.

(10) Patent No.: US 12,397,150 B2
(45) Date of Patent: Aug. 26, 2025

(54) FUNCTIONAL PROTECTOR WITH ELECTRIC CONDUCTION AND HEAT CONDUCTION

(71) Applicant: Hui-Ling Chang, Taiwan (CN)

(72) Inventors: Chien-Hung Lai, Taiwan (CN);
Chang-Sheng Wu, Taiwan (CN);
Ke-Chi Fu, Taiwan (CN);
Chung-Chuan Chang, Taiwan (CN)

(73) Assignee: Hui-Ling Chang, New Taipei (TW)

( * ) Notice: Subject to any disclaimer, the term of this patent is extended or adjusted under 35 U.S.C. 154(b) by 407 days.

(21) Appl. No.: 17/923,200

(22) PCT Filed: Jun. 9, 2020

(86) PCT No.: PCT/CN2020/095129
§ 371 (c)(1),
(2) Date: Nov. 3, 2022

(87) PCT Pub. No.: WO2021/248313
PCT Pub. Date: Dec. 16, 2021

(65) Prior Publication Data
US 2023/0181895 A1    Jun. 15, 2023

(51) Int. Cl.
*A61N 1/04* (2006.01)
(52) U.S. Cl.
CPC .................. *A61N 1/0472* (2013.01)
(58) Field of Classification Search
CPC .. A61N 1/0472; A61N 1/0452; A61N 1/0456; A61N 1/0484; A61N 1/0492
See application file for complete search history.

(56) References Cited

U.S. PATENT DOCUMENTS 6,228,206 B1 * 5/2001 Herman ............... A61N 1/0436
156/291
2004/0237170 A1 * 12/2004 Yamazaki ............ A41D 19/015
2/159

(Continued)

FOREIGN PATENT DOCUMENTS

CN    209490384 U    10/2019
TW    M583297 U    9/2019

(Continued)

OTHER PUBLICATIONS

Search Report dated Mar. 10, 2021 of the corresponding PCT patent application No. PCT/CN2020/095129.

(Continued)

*Primary Examiner* — Scott M. Getzow
(74) *Attorney, Agent, or Firm* — Chun-Ming Shih; HDLS IPR SERVICES (57) ABSTRACT

The present disclosure discloses a functional protector with electric conduction and heat conduction including a body, a conductive cloth and at least one electrode connection part. The body is an elastic stretch cloth. At least one joint part is arranged on the body. The conductive cloth is arranged on one side of the body. A conducting wire and at least one electrode part electrically connected to the conducting wire are arranged on the conductive cloth. The electrode connection parts are arranged on the body, through the body and electrically connected to the conductive cloth. Moreover, the electrode connection part transmits signals onto the conductive cloth, so that the electrode part of the conductive cloth generates an effect of an electrotherapy or a thermotherapy, or both the electrotherapy and the thermotherapy simultaneously.

10 Claims, 9 Drawing Sheets

(56) References Cited

U.S. PATENT DOCUMENTS

2013/0006335 A1* 1/2013 Lowe .................. A61H 9/0092
                                                      607/104
2016/0331959 A1* 11/2016 Hsieh ........................ A61F 7/02
2019/0234706 A1* 8/2019 Deveau ................. A41D 19/01

FOREIGN PATENT DOCUMENTS

| TW | M583305 U | 9/2019 |
| TW | I685598 B | 2/2020 |
| TW | M602412 U | 10/2020 |
| WO | 2019143307 A2 | 7/2019 |

OTHER PUBLICATIONS

Office Action dated Dec. 13, 2021 of the corresponding Taiwan patent application No. 109118025.

* cited by examiner

FUNCTIONAL PROTECTOR WITH ELECTRIC CONDUCTION AND HEAT CONDUCTION

CROSS-REFERENCE TO RELATED APPLICATION

This application is the National Phase of PCT International Application No. PCT/CN2020/095129 filed on Jun. 9, 2020. The entire disclosures of the above application are all incorporated herein by reference.

BACKGROUND OF THE DISCLOSURE

Technical Field

The present disclosure relates to a fabric structure, and especially relates to a wearable functional protector with electric conduction and heat conduction.

Description of Related Art

It is known that currently the common sport injuries, degeneration or other problems, with the use of 3C electronic products leading to many bad postures, result in physical pain, such as soreness, pain, numbness and other symptoms due to prolonged bowing and hunchback causing muscle imbalance. Patients will firstly use patches, anti-inflammatory pain relievers or massages to relieve pain once these symptoms occur. However, these methods may not completely cure these symptoms, so patients will seek professional treatment from a physical therapist, or under the evaluation of the physical therapist, patients can purchase physical therapy instruments or apparatuses to use electrotherapy or thermotherapy by themselves.

In the past, these apparatuses for electrotherapy or thermotherapy have a protector and a low frequency therapy apparatus. After the low frequency therapy apparatus is electrically connected to the protector, the current generated by the low frequency therapy apparatus is transmitted to the protector, so that the electrode part on the protector can perform physical therapy on the sore place of the patient. Because some protector products are mostly conductive textiles on the whole surface (such as Taiwan Patent Certificate number I685598, M583305 and M583297), performing electrotherapy and thermotherapy for specific small areas and pathological parts is impossible. Some protectors are made of stretch elastic cloth, so some electrode materials cannot be used on stretchable wearing apparatuses (protectors) when the some electrode materials are extended; because the electrode material itself is relatively fragile, when used in electrotherapy and thermotherapy products, the electrode material is easy to crack and does not smoothly stick to the skin thus causing allergies and burns.

SUMMARY OF THE DISCLOSURE

The main object of the present disclosure is to solve the conventional deficiencies.

In order to achieve the object mentioned above, the present disclosure provides a functional protector with electric conduction and heat conduction including a body, a conductive cloth, at least one electrode connection part and at least one joint part. The body is an elastic stretch cloth. The at least one joint part is arranged on the body. The conductive cloth is arranged on one side of the body. A conducting wire and at least one electrode part electrically connected to the conducting wire are arranged on the conductive cloth; namely, the conductive cloth includes a conducting wire (arranged on the body) and at least one electrode part (electrically connected to the conducting wire and arranged on the body). The electrode connection parts are arranged on the body, through the body and electrically connected to the conductive cloth. Moreover, the electrode connection part transmits signals onto the conductive cloth, so that the electrode part of the conductive cloth generates an effect of (namely, performs) an electrotherapy or a thermotherapy, or both the electrotherapy and the thermotherapy simultaneously.

In an embodiment of the present disclosure, the conductive cloth is a silver fiber cloth, a fabrication of nanometer silver wires or a printing of a conductive paste.

In an embodiment of the present disclosure, the conductive paste is a thermal-transfer-type conductive gel.

In an embodiment of the present disclosure, the conductive cloth is made of the conductive paste printed on an organic hot melt adhesive.

In an embodiment of the present disclosure, the electrode part of the conductive cloth is a hollow-shaped structure with dot-shaped pores, strip-shaped pores or mesh-shaped pores.

In an embodiment of the present disclosure, the functional protector is a wrist band.

In an embodiment of the present disclosure, the body has (namely, defines) a through hole which the joint part is through. A Velcro tape is arranged on one side of the joint part; namely, the functional protector further includes a Velcro tape arranged on one side of the joint part.

In an embodiment of the present disclosure, the body is a butterfly-shaped knee pad. Two joint parts are arranged on a wing at one side of the butterfly-shaped knee pad; namely, the functional protector includes two joint parts arranged on a wing at one side of the butterfly-shaped knee pad. A Velcro tape is arranged on one side of each of the two joint parts; namely, the functional protector further includes a Velcro tape arranged on one side of each of the two joint parts.

In an embodiment of the present disclosure, at least one group of the conducting wires and the electrode parts included in the conductive cloth is arranged radially on the body. A central position to which the conducting wires (of the at least one group of the conducting wires and the electrode parts included in the conductive cloth arranged radially on the body) are connected is electrically connected to the electrode connection part.

In an embodiment of the present disclosure, the body is a butterfly-shaped shoulder pad. The butterfly-shaped shoulder pad includes two shoulder straps. The two shoulder straps are arranged symmetrically at two wings of two sides of the butterfly-shaped shoulder pad respectively.

In an embodiment of the present disclosure, two upper and two lower groups of the conducting wire and the electrode part included in the conductive cloth are arranged on an inner surface of the butterfly-shaped shoulder pad. A connecting point to which the conducting wires (of the two upper or the two lower groups of the conducting wire and the electrode part included in the conductive cloth) are connected is electrically connected to the electrode connection part.

Besides, the present disclosure uses a conductive material, such as silver fiber cloth, nanometer silver wires, thermal-transfer-type conductive gel, conductive paste or printed conductive gel, to manufacture the conductive cloth; then the conductive cloth is variously cut and then fixed on the body of the protector by various fixing methods, such as pasting after back glue, hot pressing after back glue, high frequency bonding, sewing and so on. The specific pattern of the conductive cloth is used as an electrotherapy electrode or a heating sheet for thermotherapy, to treat sub-healthy people and patients or to train specific muscles, to relieve pain, strengthen the human body and so on.

Besides, another object of the present disclosure is to use a single or a small amount of designed conductive patterns to meet various physiques of the masses, for example, the fatter people and the thinner people, who may achieve/have the same therapeutic effect.

DETAILED DESCRIPTION

Figure 1:
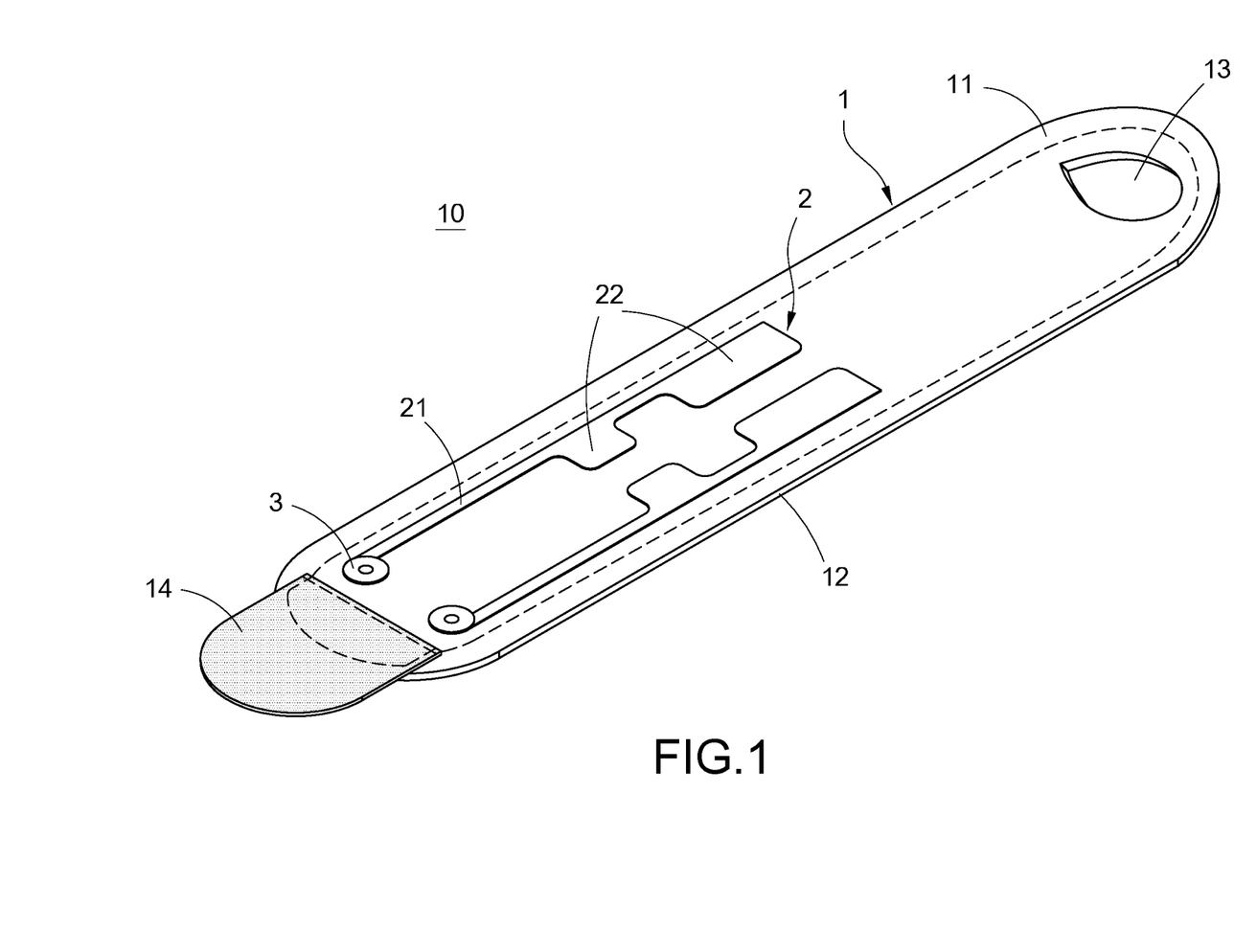
FIG. 1 shows a three-dimensional schematic diagram of the appearance of the first embodiment of the protector of the present disclosure.
Figure 2:
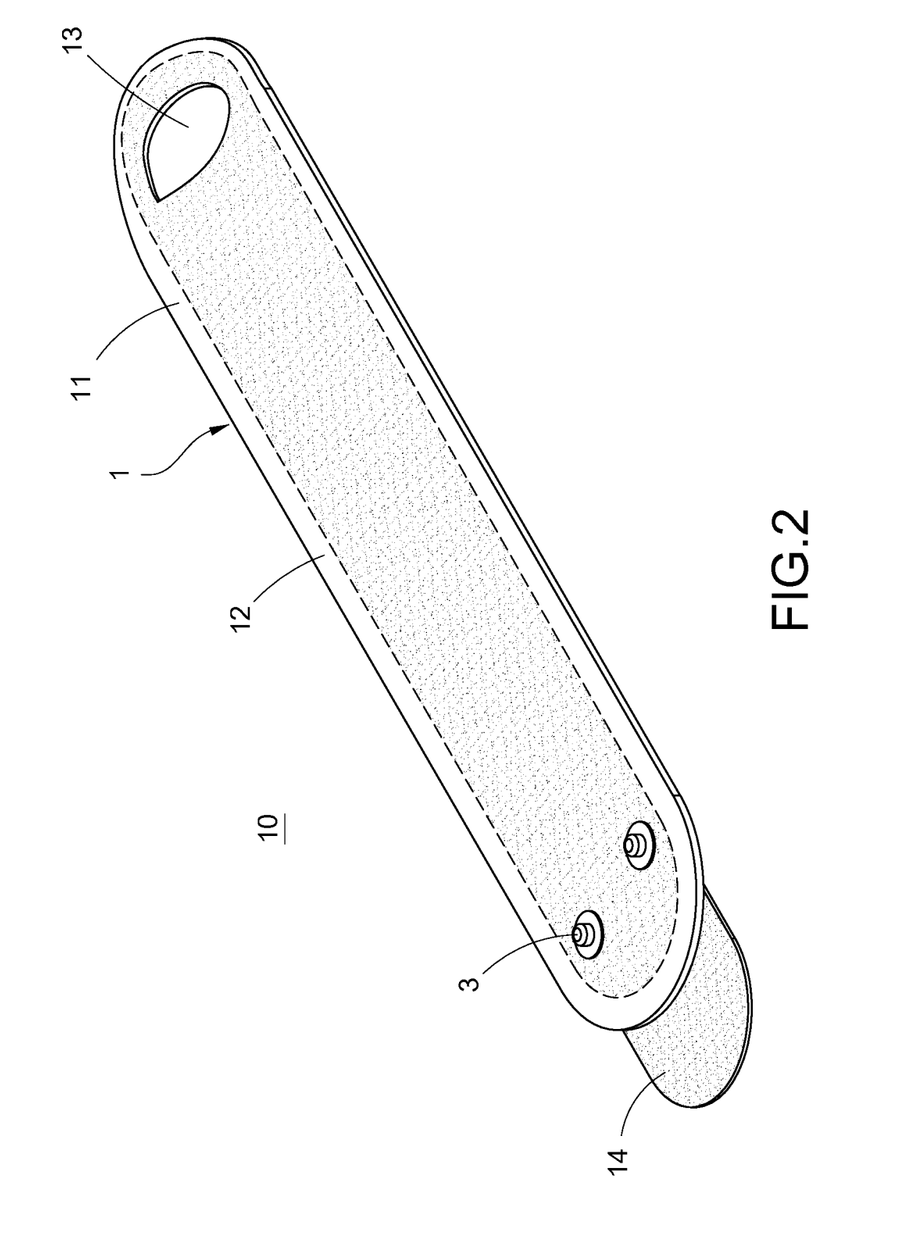
FIG. 2 shows a schematic diagram of the outer surface of FIG. 1.
Figure 3:
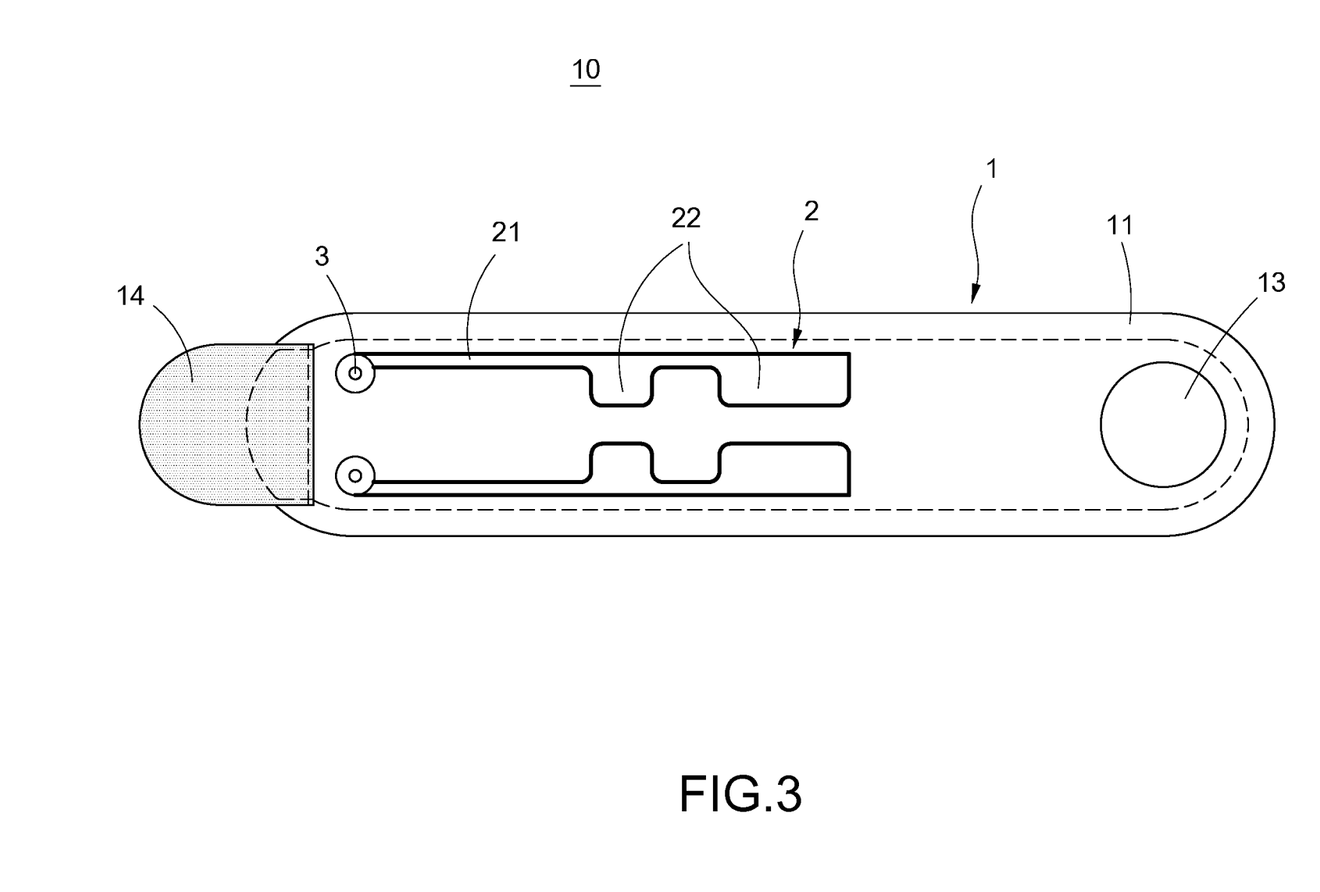
FIG. 3 shows a schematic diagram of a top view of FIG. 1.

Regarding the technical contents and detailed descriptions of the present disclosure, it is now described with the drawings as follows:

FIG. 1 shows a three-dimensional schematic diagram of the appearance of the first embodiment of the protector of the present disclosure. FIG. 2 shows a schematic diagram of the outer surface of FIG. 1. FIG. 3 shows a schematic diagram of a top view of FIG. 1. As shown in FIG. 1, FIG. 2 and FIG. 3, a protector 10 of the present disclosure includes a body 1, a conductive cloth 2, at least one electrode connection part 3 and at least one joint part 14. The protector 10 is connected to an external low frequency electrotherapy-thermotherapy apparatus, so that the electrotherapy or the thermotherapy may be performed, or both the electrotherapy and the thermotherapy may be performed simultaneously.

The body 1 is an elastic stretch cloth. In the embodiment, the body 1 is manufactured as a protective apparatus of an elongated wrist strap, and includes an inner surface 11 and an outer surface 12. The body 1 has (namely, defines) a through hole 13 at one end of the body 1 while the joint part 14 is arranged at the other end of the body 1. After the body 1 is wrapped around the wrist and the joint part 14 is through the through hole 13, a Velcro tape (not shown in the figures) arranged on one side of the joint part 14 is bonded to the surface of the body 1, so that the body 1 may be wrapped around the wrist for use. In the embodiment, the body 1 is an adhesive cloth (such as an adhesive bandage), a non-adhesive bandage or a high-elastic elastic stretch cloth; the elastic stretch cloth is a conventional three-layer sandwich cloth material, which sequentially includes but not limited to a first layer of lint-free nylon brush cloth (OK cloth), a second layer of styrene butadiene rubber (SBR) and a third layer of nylon fiber material.

The conductive cloth 2 is a silver fiber cloth, which is elastic and has a certain tensile strength. The interwoven silver fiber cloth has more strength, is not easy to break and is not easy to lose the conductive function. During production, the silver fiber cloth is subject to various cutting processes, and then fixed on one side of the body 1 (for example, the inner surface 11 of the body 1) by various fixing methods, such as pasting after back glue, hot pressing after back glue, high frequency bonding, sewing and so on. A conducting wire 21 and at least one electrode part 22 electrically connected to the conducting wire 21 are arranged on the conductive cloth 2; namely, the conductive cloth 2 includes a conducting wire 21 (arranged on the body 1) and at least one electrode part 22 (electrically connected to the conducting wire 21 and arranged on the body 1). The conducting wire 21 is used to transmit currents, and a specific pattern of the electrode part 22 is used as an electrotherapy electrode or a heating sheet for thermotherapy, to treat sub-healthy people (meaning that people are in a critical state between health and disease, and people's mind or body is in chaos, but there is no obvious pathological characteristic) and patients or to train specific muscles, to relieve pain, strengthen the human body and so on. Moreover, the conductive cloth 2 is designed with a single or a small number of conductive patterns to meet various physiques of the masses, for example, the fatter people and the thinner people, who may achieve/have the same therapeutic effect. In the embodiment, the conductive cloth 2 is F-shaped. In addition to silver fiber cloth, a fabrication of nanometer silver wires or a printing of a conductive paste may also be used for the conductive cloth 2. In some embodiments, the conductive paste is a thermal-transfer-type conductive gel. In some embodiments, the conductive cloth 2 is made of the conductive paste printed on an organic hot melt adhesive.

The electrode connection part 3 is arranged on the body 1, through the inner surface 11 and the outer surface 12 of the body 1, and electrically connected to the conductive cloth 2. After the electrode connection part 3 is electrically connected to the electro-thermal medical apparatus (not shown in the figures), with the output current, the electrode part 22 generates the effect of the electrotherapy or the thermotherapy, or both the electrotherapy and the thermotherapy simultaneously. In the embodiment, the electrode connection part 3 is a male connector of a button.

Figure 4:
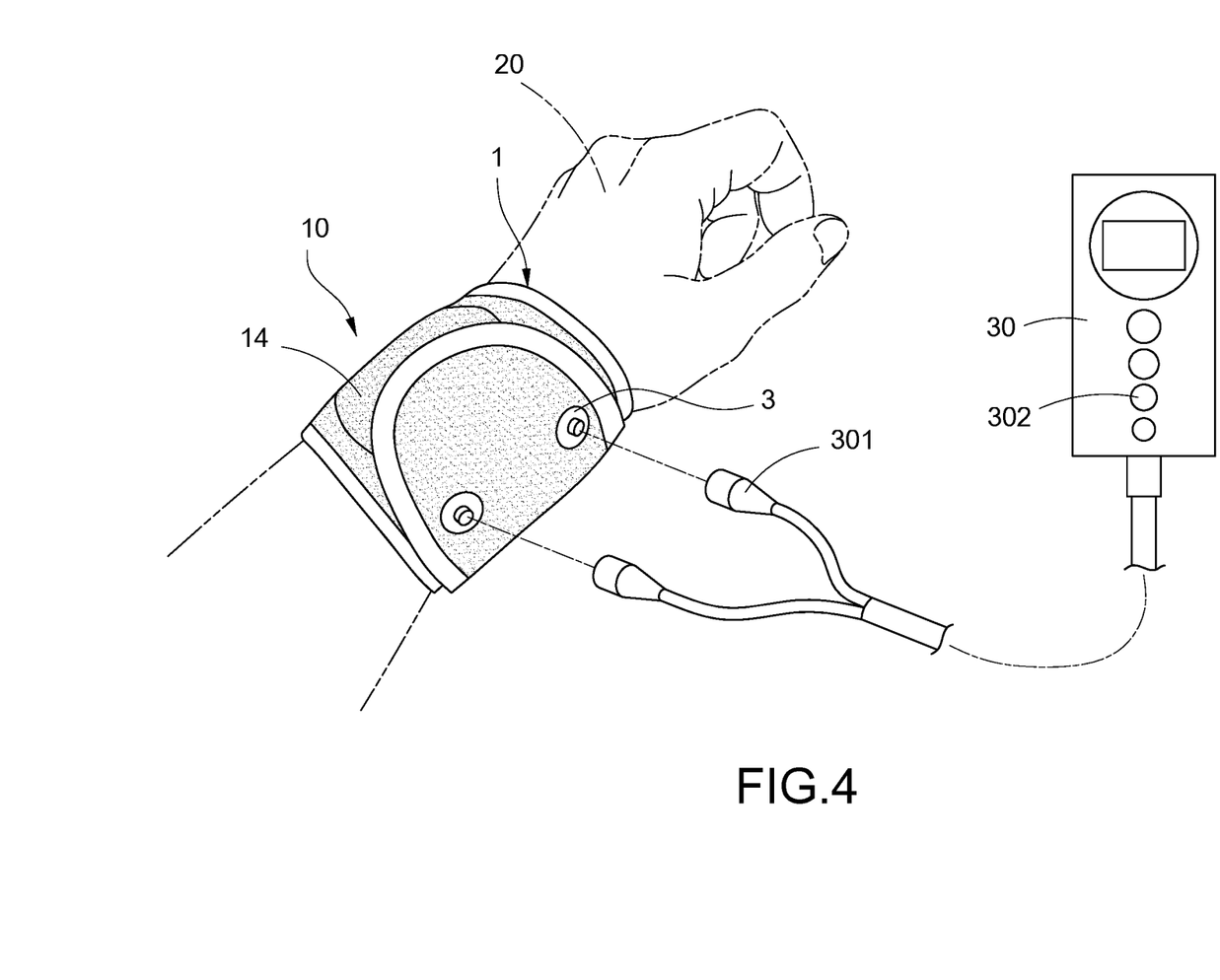
FIG. 4 shows a schematic diagram of the state in which the protector of FIG. 1 is used together with the electro-thermal medical apparatus.

FIG. 4 shows a schematic diagram of the state in which the protector of FIG. 1 is used together with the electro-thermal medical apparatus. As shown in FIG. 4, when the protector 10 of the present disclosure is a wrist bracer or a wrist band, the body 1 of the protector 10 is wrapped around the wrist of the hand 20; after the joint part 14 arranged at the other end of the body 1 is through the through hole 13, a Velcro tape (not shown in the figures) arranged on one side of the joint part 14 is bonded to the surface of the body 1, so that the body 1 may be wrapped around the wrist.

After the protector 10 is wrapped around the wrist, the electrode connection part 3 is exposed on one side of the body 1. An electrode connector 301 of an electro-thermal medical apparatus 30 is electrically connected onto the electrode connection part 3. After a button 302 of the electro-thermal medical apparatus 30 is pressed, the current outputted by the electro-thermal medical apparatus 30 is transmitted onto the electrode connection part 3 through the electrode connector 301, and then the current is transmitted onto the conductive cloth 2 by the electrode connection part 3, so that the electrode part 22 of the conductive cloth 2 can perform the treatment course of the electrotherapy or the thermotherapy, or both the electrotherapy and the thermotherapy simultaneously.

Figure 5:
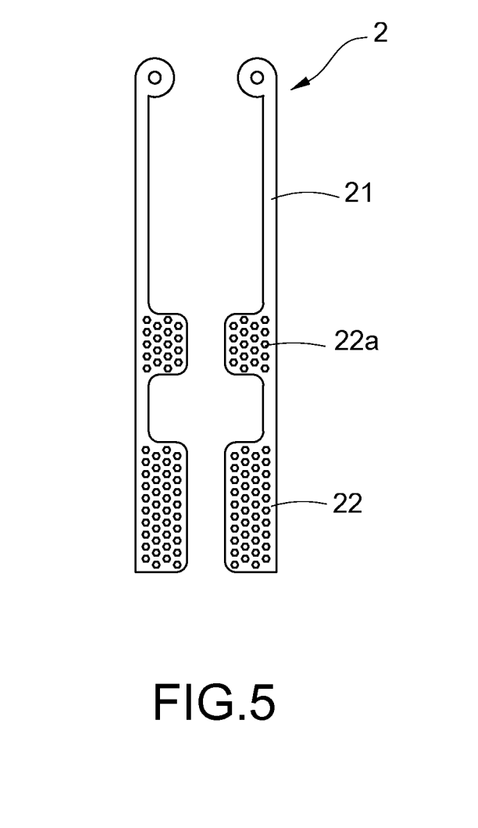
FIG. 5 shows a schematic diagram of another embodiment of the conductive cloth of the protector of the present disclosure.
Figure 6:
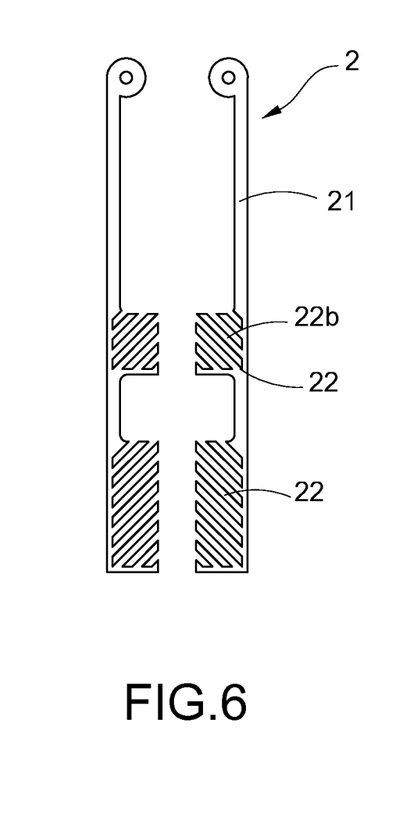
FIG. 6 shows a schematic diagram of yet another embodiment of the conductive cloth of the protector of the present disclosure.
Figure 7:
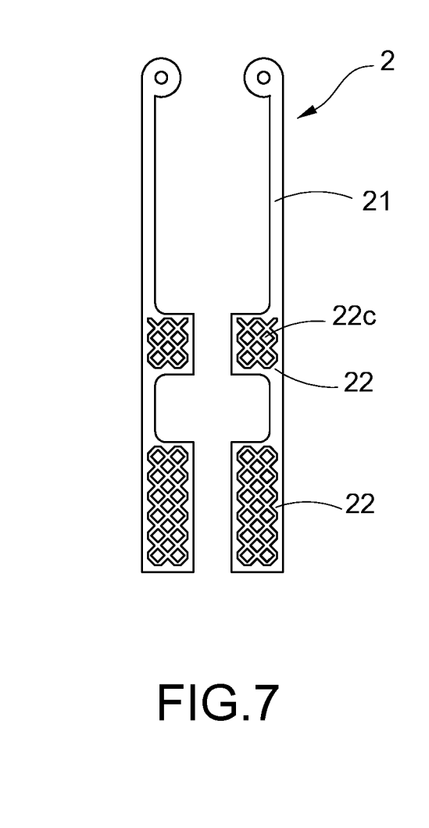
FIG. 7 shows a schematic diagram of still another embodiment of the conductive cloth of the protector of the present disclosure.

FIG. 5, FIG. 6 and FIG. 7 show schematic diagrams of various embodiments of the conductive cloth of the protector of the present disclosure. As shown in FIG. 5, FIG. 6 and FIG. 7, the conductive cloth 2 of the present disclosure is made of silver fiber cloth, nanometer silver wires, thermal-transfer-type conductive gel or printed conductive paste. When the conductive cloth 2 is processed, the electrode part 22 of the conductive cloth 2 may be designed as a hollow-shaped structure with various pore shapes such as dot-shaped pores 22a, strip-shaped pores 22b, mesh-shaped pores 22c and so on. The electrode part 22 is fixed on the body 1 of the protector 10 by adhesion, thermal transfer, printing or other techniques. Since the conductive cloth 2 is a hollow-shaped structure with dot-shaped pores 22a, strip-shaped pores 22b or mesh-shaped pores 22c, the body 1 (such as the bottom fabric) has high elasticity and better stretching performance. When the body 1 is stretched, the conductive cloth 2 will not be broken due to insufficient interlayer adhesion and tension, and will not lose conductive performance.

Figure 8:
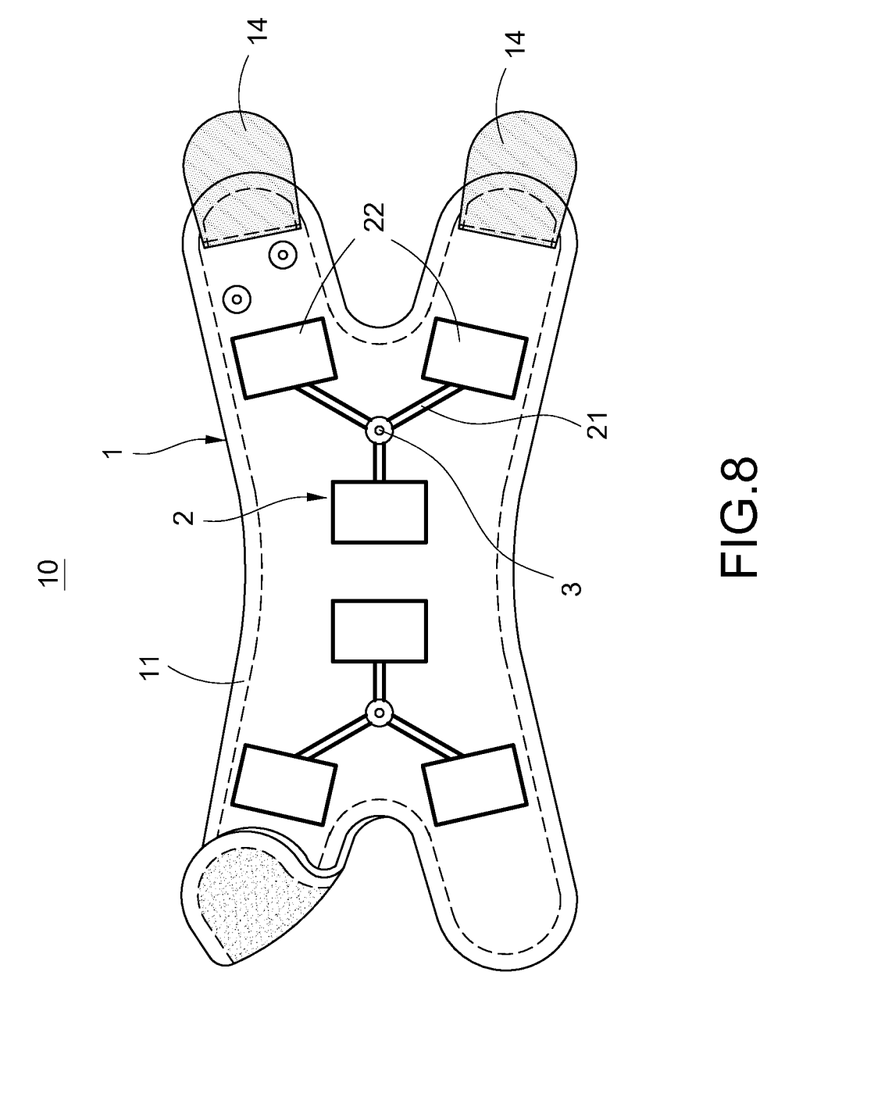
FIG. 8 shows a three-dimensional schematic diagram of the appearance of the second embodiment of the protector of the present disclosure.
Figure 9:
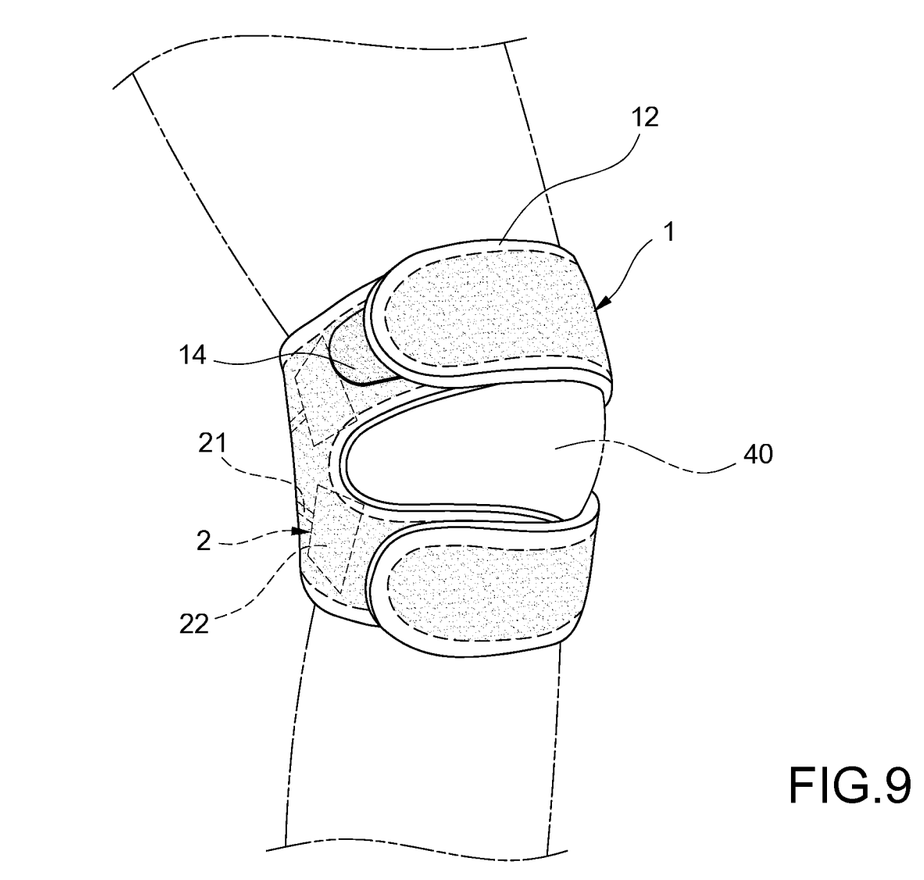
FIG. 9 shows a schematic diagram of the state in which the protector of FIG. 8 is used.

FIG. 8 shows a three-dimensional schematic diagram of the appearance of the second embodiment of the protector of the present disclosure. FIG. 9 shows a schematic diagram of the state in which the protector of FIG. 8 is used. As shown in FIG. 8 and FIG. 9, this embodiment is substantially the same as the first embodiment, except that: the body 1 of the protector 10 is made into a butterfly shape; two symmetrical joint parts 14 are arranged on a wing at one side of the body 1; a Velcro tape (not shown in the figures) is arranged on one side of each of the two joint parts 14 to bonded to the outer surface 12 of the body 1, so that the body 1 may be wrapped around the knee 40.

Two groups of the conducting wires 21 and the electrode parts 22 included in the conductive cloth 2 are arranged radially on the inner surface 11 of the body 1. A central position to which the conducting wires 21 (arranged radially on the inner surface 11 of the body 1) are connected is electrically connected to the electrode connection part 3.

When the butterfly-shaped protector 10 is used, the body 1 is wrapped around from the back of the knee 40 to the front of the knee 40; the Velcro tape arranged on one side of each of the two joint parts 14 is bonded to the outer surface 12 of the body 1, so that the body 1 of the protector 10 may be wrapped around the knee 40. After the protector 10 is wrapped around the knee 40, the electrode connector 301 of the electro-thermal medical apparatus 30 (which is the same as that of FIG. 4) is electrically connected onto the electrode connection part 3. After the button 302 of the electro-thermal medical apparatus 30 is pressed, the current outputted by the electro-thermal medical apparatus 30 is transmitted onto the electrode connection part 3 through the electrode connector 301, and then the current is transmitted onto the conductive cloth 2 by the electrode connection part 3, so that the electrode part 22 of the conductive cloth 2 can perform the treatment course of the electrotherapy or the thermotherapy, or both the electrotherapy and the thermotherapy simultaneously, on the knee 40 of the patient.

Figure 10:
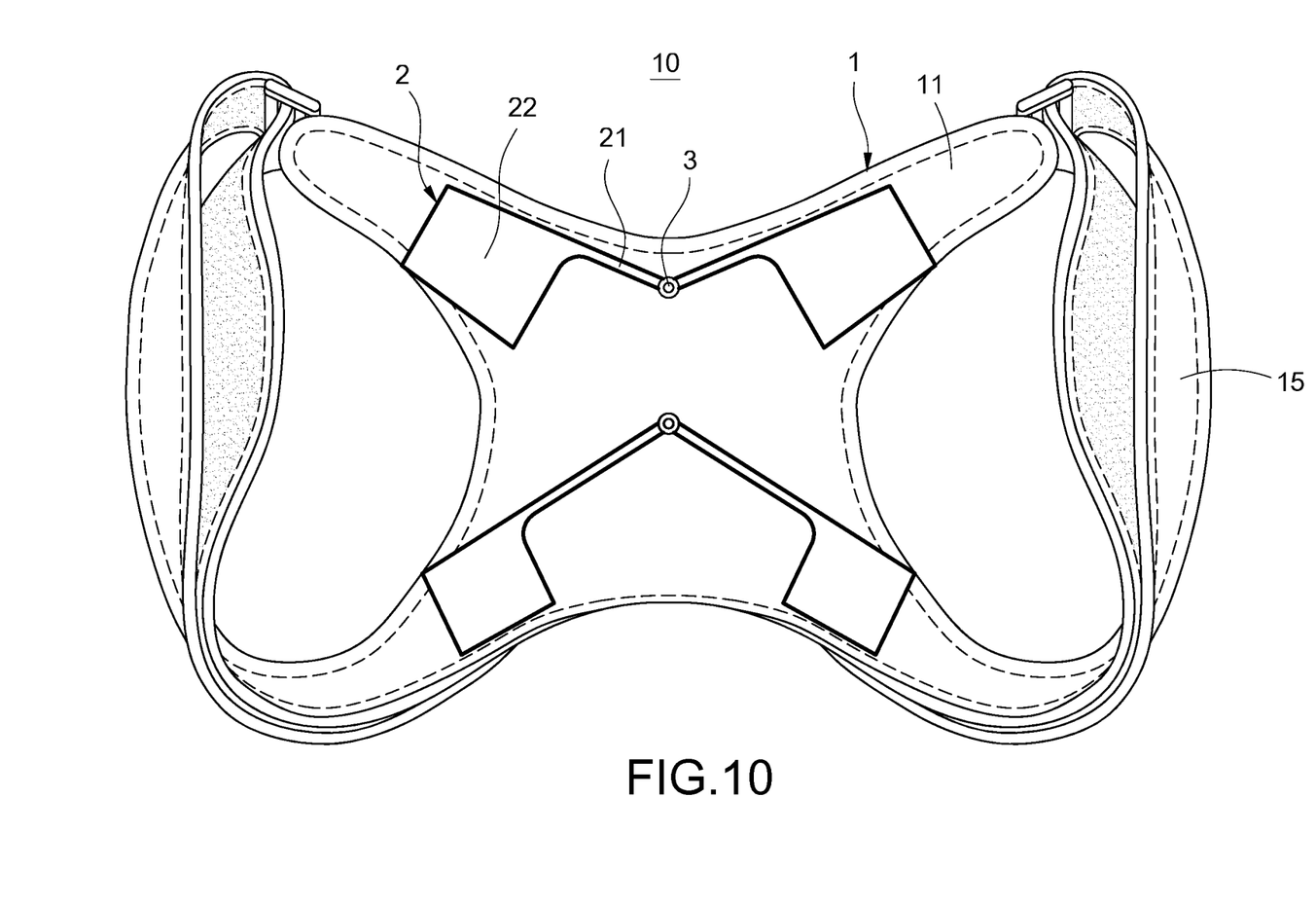
FIG. 10 shows a three-dimensional schematic diagram of the appearance of the third embodiment of the protector of the present disclosure.
Figure 11:
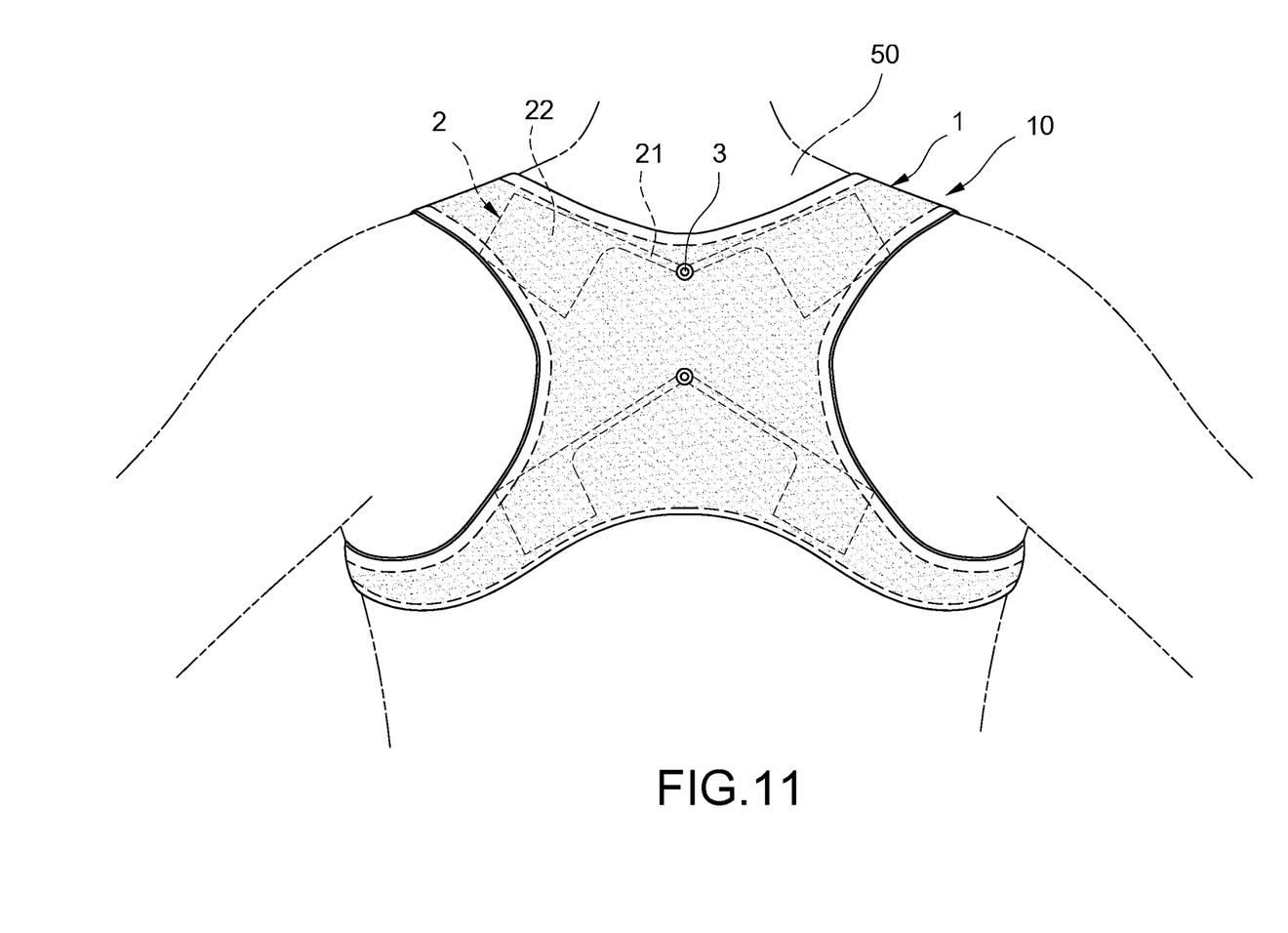
FIG. 11 shows a schematic diagram of the state in which the protector of FIG. 10 is used.

FIG. 10 shows a three-dimensional schematic diagram of the appearance of the third embodiment of the protector of the present disclosure. FIG. 11 shows a schematic diagram of the state in which the protector of FIG. 10 is used. As shown in FIG. 10 and FIG. 11, this embodiment is substantially the same as the first embodiment or the second embodiment, except that: the protective 10 is manufactured so as to include the body 1 in a shape of a butterfly with area large enough for wrapping on human torso; two shoulder straps 15 which are symmetric and can be reset in size are arranged on two wings at two sides of the body 1 respectively; the two shoulder straps 15 can be worn on the shoulder fossae or the scapulae of the back 50 of the user. Two upper and two lower groups of the conducting wire 21 and the electrode part 22 included in the conductive cloth 2 are arranged on the inner surface 11 of the body 1. A connecting point to which the conducting wires 21 (of the two upper or the two lower groups of the conducting wire 21 and the electrode part 22 included in the conductive cloth 2 arranged on the inner surface 11 of the body 1) are connected is electrically connected to the electrode connection part 3.

When the shoulder pad is used, two arms pass through the two shoulder straps 15 respectively, and then the body 1 may be worn on the shoulder fossae or the scapulae of the back 50. The electrode connector 301 of the electro-thermal medical apparatus 30 (which is the same as that of FIG. 4) is electrically connected onto the electrode connection part 3. After the button 302 of the electro-thermal medical apparatus 30 is pressed, the current outputted by the electro-thermal medical apparatus 30 is transmitted onto the electrode connection part 3 through the electrode connector 301, and then the current is transmitted onto the conductive cloth 2 by the electrode connection part 3, so that the electrode part 22 of the conductive cloth 2 can perform the treatment course of the electrotherapy or the thermotherapy, or both the electrotherapy and the thermotherapy simultaneously.

With the design of the structure of the protector 10 of the present disclosure mentioned above, the protector 10 is used in the electrotherapy and the thermotherapy; applicable products of the protector 10 includes related protectors, clothing textiles, diabetic care socks, migraine care headbands, thermotherapy and electrotherapy knee pads, wrist bands for De-Quervain's Disease and posture correction strap; or applicable products of the protector 10 includes related protectors, clothing textiles, functional sport clothing, muscle training clothing for electronic muscle stimulation (EMS) or heart rate monitoring clothing in electrocardiograph signal system, electromyography signal system and rehabilitation monitoring system.

The descriptions mentioned above are only the embodiments of the present disclosure, and are not intended to limit the scope of the present disclosure. Therefore, any equivalent changes made by using the contents of the descriptions or drawings of the present disclosure are equally included in the scope of the present disclosure.

What is claimed is:

1. A functional protector with electric conduction and heat conduction, the functional protector comprising:
    a body, wherein the body is an elastic stretch cloth;
    a joint part arranged on one end of the body;
    a conductive cloth arranged on one side of the body and comprising a conducting wire and at least one electrode part electrically connected to the conducting wire; and at least one electrode connection part arranged on the body, through the body and electrically connected to the conductive cloth, wherein the electrode connection part is configured to transmit a current onto the conductive cloth, so that the electrode part of the conductive cloth is configured to generate an effect of an electrotherapy or a thermotherapy, or both the electrotherapy and the thermotherapy simultaneously;

wherein the body defines a through hole which the joint part is through; the functional protector further comprises a Velcro tape arranged on one side of the joint part.

2. The functional protector of claim 1, wherein the conductive cloth is a silver fiber cloth, a fabrication of nanometer silver wires or a printing of a conductive paste.

3. The functional protector of claim 2, wherein the conductive paste is a thermal-transfer-type conductive gel.

4. The functional protector of claim 2, wherein the conductive cloth is made of the conductive paste printed on an organic hot melt adhesive.

5. The functional protector of claim 1, wherein the electrode part of the conductive cloth is a hollow-shaped structure with dot-shaped pores, strip-shaped pores or mesh-shaped pores.

6. The functional protector of claim 5, wherein the body is a wrist band.

7. The functional protector of claim 1, wherein the body is a butterfly-shaped knee pad; the functional protector comprises two joint parts arranged on a wing at one side of the butterfly-shaped knee pad; the functional protector further comprises a Velcro tape arranged on one side of each of the two joint parts.

8. The functional protector of claim 7, wherein at least one group of the conducting wires and the electrode parts included in the conductive cloth is arranged radially on the body; a central position to which the conducting wires of the at least one group of the conducting wires and the electrode parts included in the conductive cloth arranged radially on the body are connected is electrically connected to the electrode connection part.

9. The functional protector of claim 1, wherein the body is a butterfly-shaped shoulder pad; the butterfly-shaped shoulder pad comprises two shoulder straps; the two shoulder straps are arranged symmetrically at two wings of two sides of the butterfly-shaped shoulder pad respectively.

10. The functional protector of claim 9, wherein two upper and two lower groups of the conducting wire and the electrode part included in the conductive cloth are arranged on an inner surface of the butterfly-shaped shoulder pad; a connecting point to which the conducting wires of the two upper or the two lower groups of the conducting wire and the electrode part included in the conductive cloth arranged on the inner surface of the butterfly-shaped shoulder pad are connected is electrically connected to the electrode connection part.

* * * * *